United States Patent
Suzuki et al.

(10) Patent No.: US 10,660,548 B2
(45) Date of Patent: May 26, 2020

(54) EVALUATION APPARATUS AND EVALUATION METHOD

(71) Applicant: TOYOTA JIDOSHA KABUSHIKI KAISHA, Toyota-shi (JP)

(72) Inventors: Kanako Suzuki, Toyota (JP); Kenichi Yamamoto, Nagoya (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 98 days.

(21) Appl. No.: 15/903,061

(22) Filed: Feb. 23, 2018

(65) Prior Publication Data

US 2018/0289290 A1 Oct. 11, 2018

(30) Foreign Application Priority Data

Apr. 10, 2017 (JP) ................................. 2017-077527

(51) Int. Cl.
| | | |
|---|---|---|
| A61H 3/00 | (2006.01) | |
| A61B 5/11 | (2006.01) | |
| A61B 5/00 | (2006.01) | |
| B25J 9/00 | (2006.01) | |
| A61H 1/02 | (2006.01) | |
| A61H 99/00 | (2006.01) | |
| G01M 99/00 | (2011.01) | |
| B25J 19/00 | (2006.01) | |

(52) U.S. Cl.
CPC .......... *A61B 5/1126* (2013.01); *A61B 5/6828* (2013.01); *A61H 1/0237* (2013.01); *A61H 1/0262* (2013.01); *A61H 3/00* (2013.01); *A61H 99/00* (2013.01); *B25J 9/0006* (2013.01); *B25J 19/0095* (2013.01); *G01M 99/007* (2013.01); *A61H 2003/005* (2013.01)

(58) Field of Classification Search
CPC ....... A61B 5/1126; A61B 5/6828; A61H 3/00; A61H 2003/005
See application file for complete search history.

(56) References Cited

U.S. PATENT DOCUMENTS

2015/0366737 A1* 12/2015 Wang ...................... A61H 1/005
601/29

FOREIGN PATENT DOCUMENTS

| CN | 102156054 A | 8/2011 |
|---|---|---|
| CN | 102841602 A | 12/2012 |
| CN | 105752197 A | 7/2016 |
| EP | 0 285 438 A2 | 10/1988 |
| JP | 2011217834 A * | 11/2011 |
| JP | 2014-147636 | 8/2014 |
| JP | 2014147636 A * | 8/2014 |

(Continued)

*Primary Examiner* — Jamel E Williams
(74) *Attorney, Agent, or Firm* — Oblon, McClelland, Maier & Neustadt, L.L.P.

(57) ABSTRACT

The present disclosure aims to provide an evaluation apparatus and an evaluation method capable of evaluating a walking assistance apparatus by simulating an actual person's walking motion. An evaluation apparatus 1 includes a placement part 5 on which a sole part of a walking assistance apparatus 4 to be evaluated is placed; an actuator 3 configured to apply a load to the walking assistance apparatus 4 in a direction of the placement part 5 in a state in which the sole part faces the placement part 5; and an actuator 6 configured to change a relative positional relation between the placement part 5 and the sole part.

12 Claims, 8 Drawing Sheets

(56) References Cited

FOREIGN PATENT DOCUMENTS

| JP | 2017-113311 | | 6/2017 |
|----|----|----|----|
| JP | 2017-143899 | | 8/2017 |
| JP | 2017143899 A | * | 8/2017 |

* cited by examiner

EVALUATION APPARATUS AND EVALUATION METHOD

CROSS REFERENCE TO RELATED APPLICATIONS

This application is based upon and claims the benefit of priority from Japanese patent application No. 2017-77527, filed on Apr. 10, 2017, the disclosure of which is incorporated herein in its entirety by reference.

BACKGROUND

The present disclosure relates to an evaluation apparatus and an evaluation method, and more specifically, to an evaluation of a walking assistance apparatus performed by applying a load to the walking assistance apparatus.

In recent years, various kinds of walking assistance apparatuses for assisting walking by patients who are suffering from, for example, paralysis due to a stroke in the acute phase have been developed. A walking assistance apparatus determines, for example, whether the user's leg is in a standing leg condition or in an idling leg condition from the user's weight that has been input and the posture of the user. The walking assistance apparatus generates torque in a knee straightening direction in order to keep the angle of the knee joint when the user's leg is in the standing leg condition. On the other hand, the walking assistance apparatus causes the user to bend the knee joint from the end of the standing leg condition to the idling leg condition to prevent the affected leg from stumbling at the time of walking, and assists walking by causing the user to swing the affected leg. The walking assistance apparatus needs to have a sufficiently high strength and durability in order to help the user to learn correct walking by performing these motions in the acute phase or at an early stage of rehabilitation. Various evaluation apparatuses for evaluating the strength and the durability of the aforementioned walking assistance apparatus have been known.

Japanese Unexamined Patent Application Publication No. 2014-147636 discloses an apparatus for evaluating the strength and the durability of a walking assistance apparatus by applying a load to the walking assistance apparatus whose sole part is placed on a surface plate placed on the floor. Japanese Unexamined Patent Application Publication No. 2014-147636 further discloses that it is possible to achieve an evaluation in which a dorsiflexion moment is reproduced by placing only a toe side of the sole of the walking assistance apparatus on the surface plate and to achieve an evaluation in which a plantar flexion moment is reproduced by placing only a heel side of the sole of the walking assistance apparatus on the surface plate.

SUMMARY

In the technique disclosed in Japanese Unexamined Patent Application Publication No. 2014-147636, one of the aspect in which the load is repeatedly applied in the state in which the whole sole of the walking assistance apparatus is placed on a placing board and the aspect in which the load is repeatedly applied in the state in which a part of the sole thereof is placed on the placing board as described above is evaluated. Therefore, it is impossible to sufficiently conduct a test in which the standing leg motion and the idling leg motion included in one walking cycle are simulated.

The present disclosure has been made in order to solve the aforementioned problem, and aims to provide an evaluation apparatus and an evaluation method capable of evaluating the walking assistance apparatus by simulating the actual person's walking motion.

An evaluation apparatus according to one aspect of the present disclosure includes: a placement part on which a sole part of a walking assistance apparatus to be evaluated is placed; load applying means for applying a load to the walking assistance apparatus in a direction of the placement part in a state in which the sole part faces the placement part; and driving means for changing a relative positional relation between the placement part and the sole part.

With the aforementioned evaluation apparatus, it is possible to apply a load while changing the relative positional relation between the placement part and the sole part of the walking assistance apparatus. It is therefore possible to evaluate the walking assistance apparatus by simulating the actual person's walking motion.

In the aforementioned aspect, the driving means may change a relative angle of the placement part and the sole part.

According to the aforementioned structure, it is possible to apply a load while changing the relative angle of the placement part and the sole part of the walking assistance apparatus. It is therefore possible to evaluate the walking assistance apparatus by simulating the actual person's walking motion.

In the aforementioned aspect, the driving means may change the relative angle of the placement part and the sole part by changing an inclination angle of the placement part.

According to the aforementioned structure, it is possible to easily change the relative angle of the placement part and the sole part.

In the aforementioned aspect, the driving means may change the inclination angle of the placement part by swinging the placement part.

According to the aforementioned structure, the change of the inclination angle of the placement part can be repeated, whereby it is possible to easily simulate the repeat of the walking motion.

In the aforementioned aspect, a placement surface of the placement part may include a movable structure.

According to the aforementioned structure, it is possible to suppress a shearing load that is generated in the walking assistance apparatus and is specific to an evaluation test. It is therefore possible to perform an evaluation in a state closer to the actual walking than the related art.

An evaluation method according to another aspect of the present disclosure is an evaluation method for evaluating a walking assistance apparatus using a placement part on which a sole part of the walking assistance apparatus to be evaluated is placed, the method including: applying a load to the walking assistance apparatus in a direction of the placement part in a state in which the sole part faces the placement part; and changing a relative positional relation between the placement part and the sole part.

In this evaluation method, it is possible to change the relative positional relation between the placement part and the sole part of the walking assistance apparatus while applying a load, whereby it is possible to evaluate the walking assistance apparatus by simulating the actual person's walking motion.

According to the present disclosure, it is possible to provide an evaluation apparatus and an evaluation method capable of evaluating the walking assistance apparatus by simulating the actual person's walking motion.

The above and other objects, features and advantages of the present disclosure will become more fully understood

DESCRIPTION OF EMBODIMENTS

Hereinafter, with reference to the drawings, an embodiment of the present disclosure will be described in detail. An evaluation apparatus according to the embodiment of the present disclosure evaluates the performance, the strength, and the durability of a walking assistance apparatus that is mounted on the user's leg part and assists the user's walking.

Figure 1:
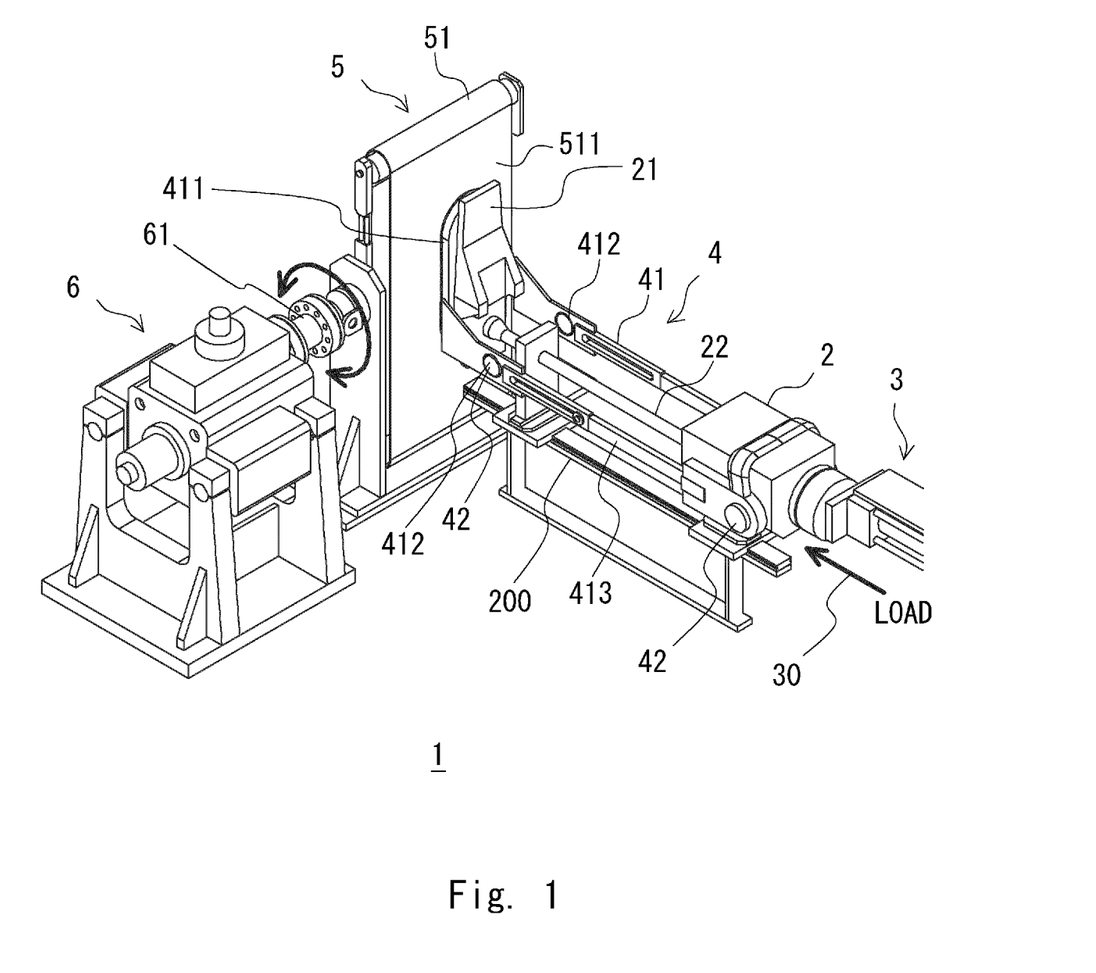
FIG. 1 is a perspective view showing a schematic configuration of an evaluation apparatus according to an embodiment.

FIG. 1 is a perspective view showing a schematic configuration of an evaluation apparatus 1 according to a first embodiment. As shown in FIG. 1, the evaluation apparatus 1 includes a dummy leg part 2 which simulates a leg part of a human, an actuator 3 for applying a weight for applying a load to the dummy leg part 2, a placement part 5, and an actuator 6 for changing the placement part that swings the placement part 5, and evaluates a walking assistance apparatus 4 mounted on the dummy leg part 2.

The dummy leg part 2 includes, for example, a rotatable joint part, and has a shape which simulates the leg part of the human. The dummy leg part 2 includes a sole part 21, which is a foot, and a lower-thigh/upper-thigh part 22 coupled to the sole part 21. The structure of the dummy leg part 2 shown in FIG. 1 is merely one example and a desired structure may be applied.

The actuator 3 is one specific example of load applying means. The actuator 3 is coupled to the lower-thigh/upper-thigh part 22 of the dummy leg part 2, and is able to apply a desired load to the dummy leg part 2. The actuator 3 is composed of, for example, a hydraulic mechanism or a motor mechanism. The actuator 3 applies a load whose direction is vertical to the sole part 21 to the dummy leg part 2.

In this embodiment, the dummy leg part 2 is arranged on a base 200 so as to overlie the base 200. The dummy leg part 2 is fixed to the base 200 in such a way that the dummy leg part 2 can slide on the base 200. Therefore, the dummy leg part 2 can be slid in the loading direction by the load applied by the actuator 3. In FIG. 1, the direction of the load applied by the actuator 3 is expressed by an arrow 30.

The walking assistance apparatus 4 is a target to be evaluated by the evaluation apparatus 1. The walking assistance apparatus 4 is mounted on the affected leg of the user and adjusts motions of the affected leg, thereby assisting walking of the affected leg. When an evaluation test is performed, the walking assistance apparatus 4 is mounted on the dummy leg part 2, as shown in FIG. 1. The walking assistance apparatus 4 includes a frame part 41 including a plurality of joint parts and a motor unit 42 that rotationally drives the joint parts of the frame part 41.

The frame part 41 is composed of a sole frame 411 and a lower-thigh/upper-thigh frame 413 coupled to the sole frame 411 via ankle joint parts 412. The sole frame 411 is mounted on the sole part 21 of the dummy leg part 2. The lower-thigh/upper-thigh frame 413 is mounted on the lower-thigh/upper-thigh part 22. The motor unit 42 is composed of, for example, a motor, a deceleration mechanism, and a sensor, and when the motor unit 42 is driven, it assists the walking by the user who wears the walking assistance apparatus 4. In this embodiment, when the evaluation test is performed, the ankle joint parts 412 are fixed so as not to be rotated. Accordingly, the state in which the sole surface of the sole frame 411 and the loading direction are substantially perpendicular to each other is maintained during the evaluation test.

The placement part 5 is a plane member on which the sole part of the walking assistance apparatus 4 to be evaluated is placed. The actuator 3 applies a load to the walking assistance apparatus 4 in the direction of the placement part 5 in a state in which the sole part of the walking assistance apparatus 4 faces the placement part 5, as shown in FIG. 1. Accordingly, the sole part of the sole frame 411 of the walking assistance apparatus 4 contacts the placement part 5.

In this embodiment, the placement part 5 includes a conveyor mechanism. More specifically, the placement part 5 is configured as a conveyor belt in which a belt 51 can be rotated. In this way, a placement surface 511 of the placement part 5 includes a movable structure.

The actuator 6 is one specific example of driving means, and changes the relative positional relation between the placement part 5 and the sole part of the walking assistance apparatus 4. In this embodiment, the actuator 6 changes the relative angle of the placement part 5 and the sole part of the walking assistance apparatus 4. Specifically, the actuator 6 is coupled to the placement part 5 via a rotation axis 61 of the actuator 6 and changes the inclination angle of the placement part 5 by the rotation of the rotation axis 61, thereby changing the relative angle of the placement part 5 and the sole part of the walking assistance apparatus 4. The actuator 6 is composed of, for example, a hydraulic mechanism or a motor mechanism.

Figure 2:
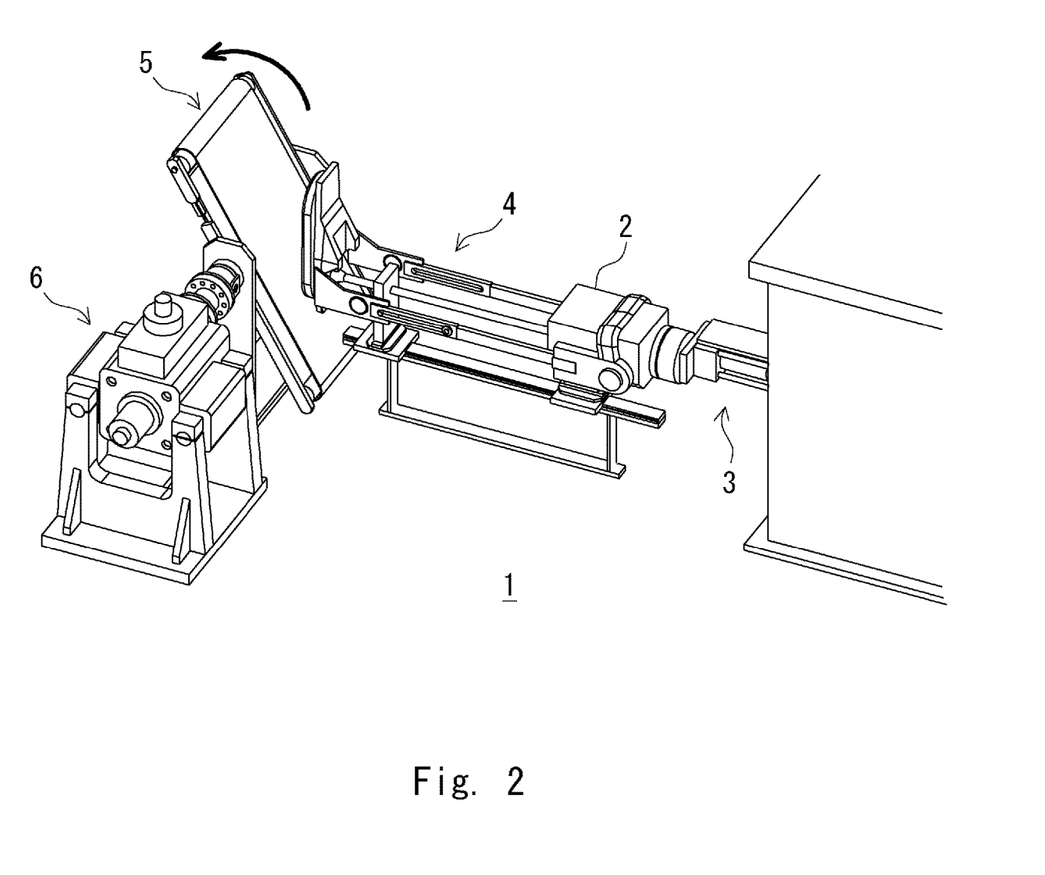
FIG. 2 is a schematic diagram showing an inclined state in which a placement surface of a placement part is inclined backward with respect to a sole part of a walking assistance apparatus.
Figure 3:
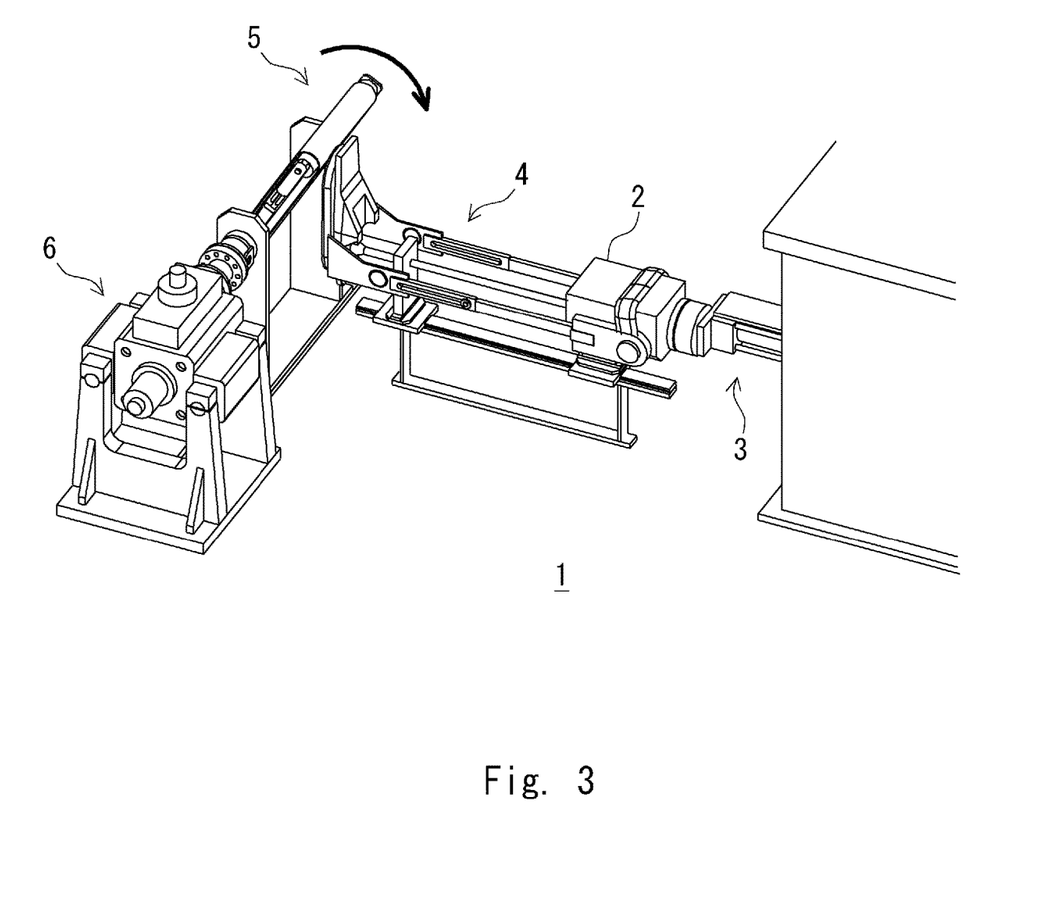
FIG. 3 is a schematic diagram showing an inclined state in which the placement surface of the placement part is inclined forward with respect to the sole part of the walking assistance apparatus.

The actuator 6 changes the inclination angle of the placement part 5 by mainly swinging the placement part 5. That is, the actuator 6 swings the placement part 5 in such a way that the inclined state in which the placement surface 511 is inclined backward with respect to the sole part of the walking assistance apparatus 4 (in other words, the inclined state in which the placement surface 511 is rotated toward the heel side of the sole frame 411) as shown in FIG. 2 and the inclined state in which the placement surface 511 is inclined forward with respect to the sole part of the walking assistance apparatus 4 (in other words, the inclined state in which the placement surface 511 is rotated toward the toe side of the sole frame 411) as shown in FIG. 3 are alternately repeated.

Figure 4:
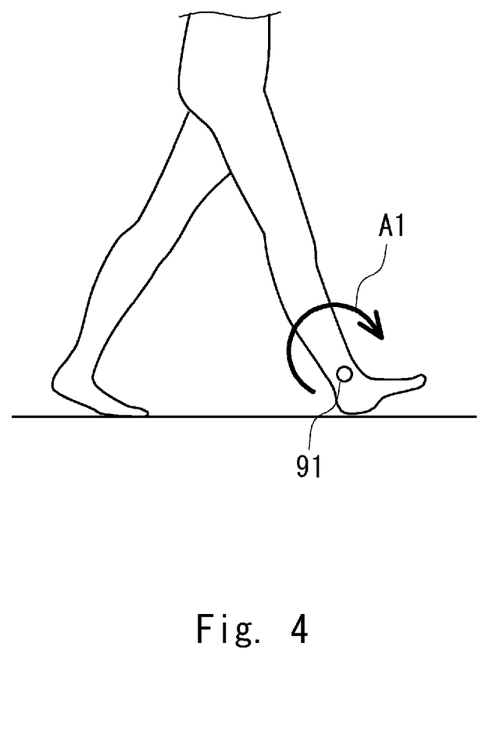
FIG. 4 is a schematic diagram showing a state in which a heel contacts the ground at the time of walking.

When the load is applied by the actuator 3 in the inclined state in which the placement surface 511 is inclined backward, a reaction force from the placement surface 511 is generated, the heel side of the sole frame 411 serving as a supporting point. It is therefore possible to reproduce the moment in the plantar flexion direction around the ankle joint parts 412 that occurs when the heel contacts the ground at the time of walking. FIG. 4 is a schematic diagram showing a state in which the heel contacts the ground at the time of walking. As shown in FIG. 4, when the heel contacts the ground, a plantar flexion motion is generated in such a way that the toe is rotated in the direction of an arrow A1, with an ankle joint 91 serving as a rotation axis. Since the load is applied by the actuator 3 in the inclined state in which the placement surface 511 is inclined backward, the load applied at the time of the plantar flexion motion is reproduced.

Figure 5:
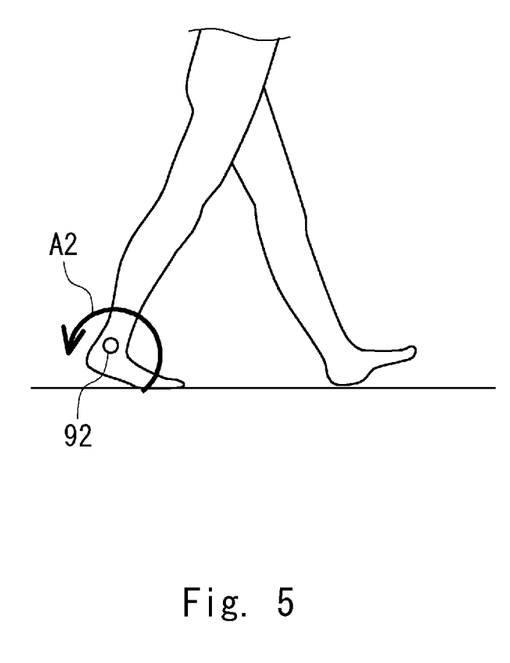
FIG. 5 is a schematic diagram showing a state in which a toe leaves the ground at the time of walking.

On the other hand, when the load is applied by the actuator 3 in the inclined state in which the placement surface 511 is inclined forward, a reaction force from the placement surface 511 is generated, the toe side of the sole frame 411 serving as a supporting point. Accordingly, it is possible to reproduce the moment in the dorsiflexion direction around the ankle joint parts 412 that occurs when the toe leaves the ground at the time of walking. FIG. 5 is a schematic diagram showing a state in which the toe leaves the ground at the time of walking. As shown in FIG. 5, when the toe leaves the ground, a dorsiflexion motion is generated in such a way that the toe is rotated in the direction of an arrow A2, with an ankle joint 92 serving as a rotation axis. Since the load is applied by the actuator 3 in the inclined state in which the placement surface 511 is inclined forward, the load applied at the time of the dorsiflexion motion is reproduced.

Figure 6:
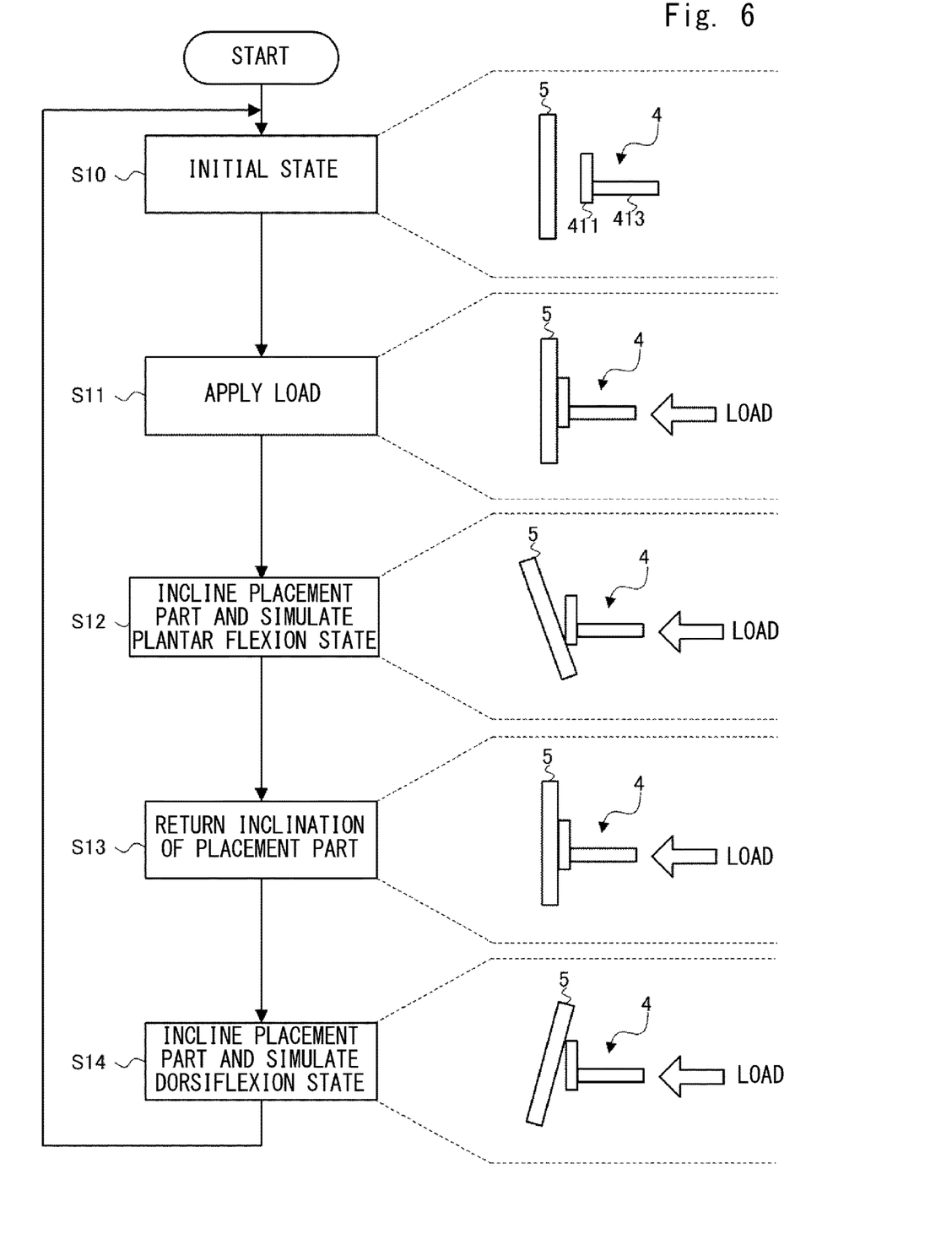
FIG. 6 is a flowchart showing one example of operations of the evaluation apparatus according to the embodiment.

Next, an operational example of the evaluation apparatus 1 will be explained. FIG. 6 is a flowchart showing one example of the operation of the evaluation apparatus 1. In the following description, with reference to FIG. 6, the operational example of the evaluation apparatus 1 will be explained. In FIG. 6, schematic diagrams indicating the respective states of the evaluation apparatus 1 in the respective steps are added to the right side of the respective steps in the flowchart.

First, the evaluation apparatus 1 is in the initial state (Step 10 (S10)). In this state, the load is not applied by the actuator 3 and the placement part 5 is not inclined by the actuator 6.

Next, in Step 11 (S11), the actuator 3 applies the load to the walking assistance apparatus 4 in the direction of the placement part 5.

Next, in Step 12 (S12), the actuator 6 inclines the placement part 5. Specifically, the actuator 6 drives to cause the placement surface 511 of the placement part 5 to be rotated toward the heel side of the sole frame 411. It is therefore possible to simulate the plantar flexion state, as described above.

Next, in Step 13 (S13), the actuator 6 returns the inclination of the placement part 5. Accordingly, the state in which the whole sole contacts the ground at the time of walking is simulated.

Next, in Step 14 (S14), the actuator 6 inclines the placement part 5 in the direction opposite to that in Step 12. Specifically, the actuator 6 drives to cause the placement surface 511 of the placement part 5 to be rotated toward the toe side of the sole frame 411. It is therefore possible to simulate the dorsiflexion state, as described above.

In the following steps, Steps 10 to 14 are repeated. It is therefore possible to alternately simulate the plantar flexion state and the dorsiflexion state. While the operations have proceeded from Steps 12, 13, and 14 in this order in the flowchart shown in FIG. 6, the operations may proceed from Steps 14, 13, and 12 in this order.

The operational example of the evaluation apparatus 1 has been described above. As will be understood from the above description, this embodiment includes an evaluation method for evaluating the walking assistance apparatus 4 using the placement part 5 on which the sole part of the walking assistance apparatus 4 to be evaluated is placed, the method including applying the load to the walking assistance apparatus 4 in the direction of the placement part 5 in the state in which the sole part of the walking assistance apparatus 4 faces the placement part 5, and changing the relative positional relation between the placement part 5 and the sole part.

Figure 7:
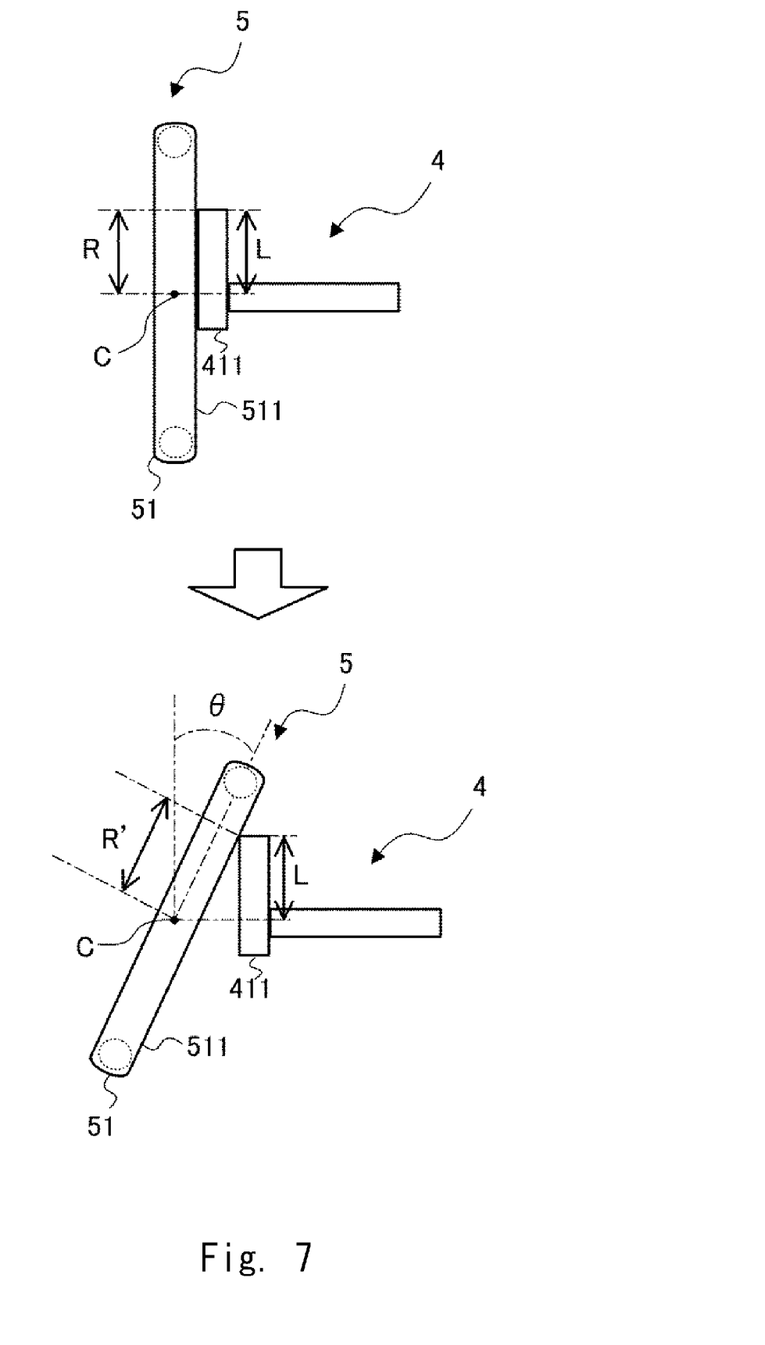
FIG. 7 is a schematic diagram for describing an amount of movement of a belt of the placement part.

When the placement part 5 is inclined, the belt 51 of the placement part 5 with which the walking assistance apparatus 4 to which the load is applied has come into contact moves in the direction of the toe or the heel due to influences of the load and the inclination of the placement part 5. FIG. 7 is a schematic diagram for describing the amount of the movement of the belt 51 of the placement part 5. In FIG. 7, L indicates the length from a rotation center C of the placement part 5 to the tip of the toe side of the sole frame 411. However, this length is a length component of the sole frame 411 in the longitudinal direction (axial direction that connects the toe and the heel), as shown in FIG. 7. Further, in FIG. 7, R and R' indicate the length from the rotation center C of the placement part 5 to the tip of the toe side of the sole frame 411. This length indicates, as shown in FIG. 7, the length component of the inclination direction of the placement part 5. The symbol R indicates the length when the inclination angle of the placement part 5 is 0, and R' indicates the length when the placement part 5 is inclined by an angle $\theta$. From these definitions, L=R is established. It is assumed here that $\Delta R = R' - R$. From the relation between R' and R, $\Delta R$ can also be expressed by $\Delta R = (1 - \cos\theta) R / \cos\theta$. When the placement part 5 is inclined by the angle $\theta$, the shearing load applied to the walking assistance apparatus 4 becomes larger in the case in which the belt 51 is not moved by $\Delta R$ than that in the case in which the belt 51 is moved thereby. That is, when the belt 51 does not move, the shearing load that does not occur in the actual walking is generated specifically in the evaluation test environment. In this embodiment, the placement surface 511 of the placement part 5 includes the movable structure, as described above. Therefore, the contact point between the sole frame 411 and the placement surface 511 can be moved on the placement surface 511 when the placement part 5 is inclined. It is therefore possible to suppress the occurrence of the shearing load applied to the walking assistance apparatus 4. That is, according to this embodiment, it is possible to simulate the state in which the toe kicks the ground in the actual walking more accurately.

Figure 8:
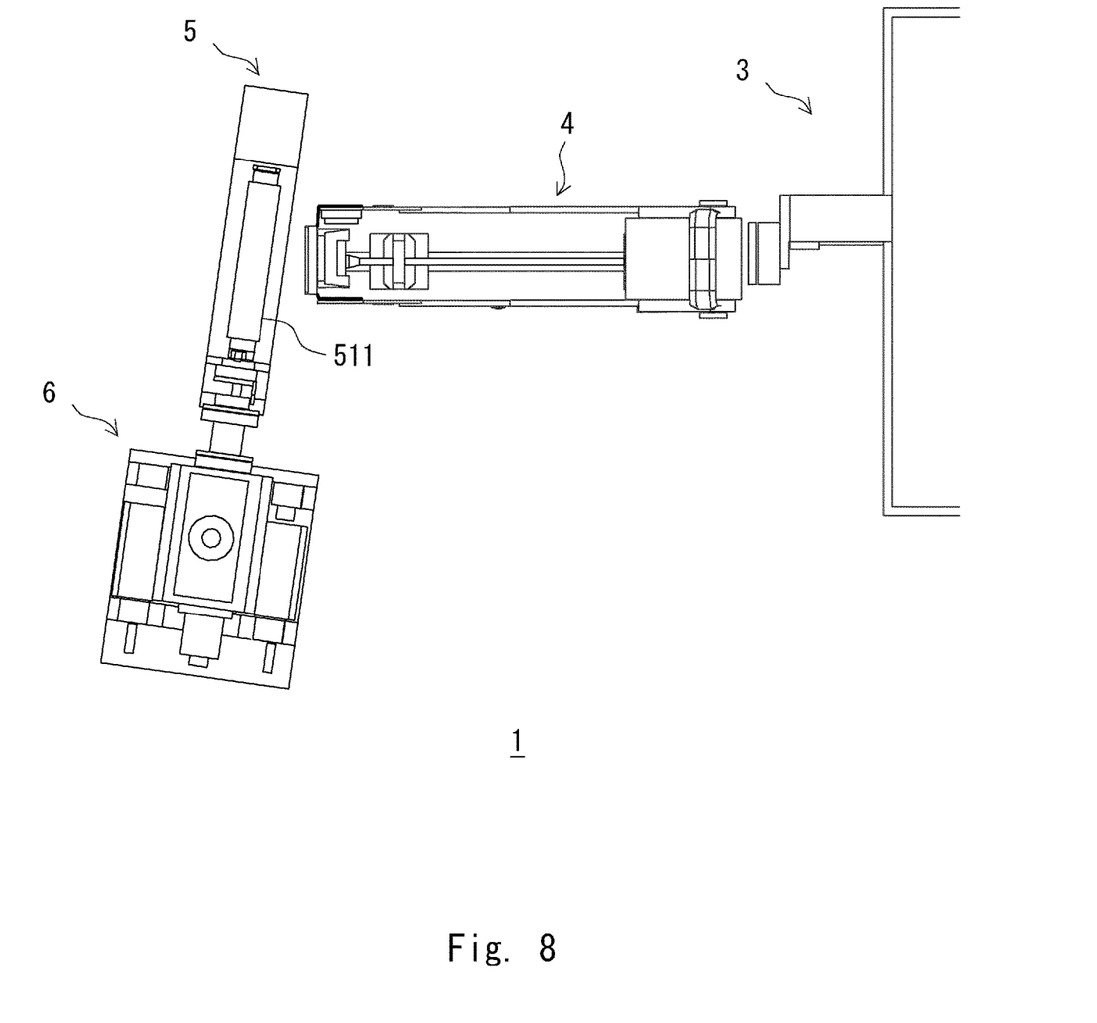
FIG. 8 is a plane view of the evaluation apparatus showing an arrangement example.

The embodiment has been described above. The evaluation apparatus 1 according to this embodiment changes the relative positional relation between the placement part 5 and the sole part of the walking assistance apparatus 4 while applying the load to the walking assistance apparatus 4 in the direction of the placement part 5 in the state in which the sole part of the walking assistance apparatus 4 faces the placement part 5. Accordingly, the vector direction of the reaction force from the placement surface 511 changes with time, whereby it is possible to simulate the plantar flexion state and the dorsiflexion state. That is, it is possible to evaluate the walking assistance apparatus by simulating the actual person's walking motion. While the placement part 5 and the walking assistance apparatus 4 may be arranged in such a way that the placement surface 511 becomes substantially parallel to the sole surface of the sole part of the walking assistance apparatus 4 (that is, the sole surface of the sole frame 411) when it is seen from the toe side of the walking assistance apparatus 4, the placement part 5 and the walking assistance apparatus 4 may be arranged in such a way that the placement surface 511 becomes inclined with respect to the sole surface of the sole part of the walking assistance apparatus 4 when it is seen from the toe side of the walking assistance apparatus 4, as shown in FIG. 8. The evaluation apparatus 1 is arranged in the state in which the placement surface 511 is thus inclined, whereby the user's walking whose center of gravity is eccentric can be simulated.

Note that the present disclosure is not limited to the aforementioned embodiment and may be changed as appropriate without departing from the spirit of the present disclosure. For example, while the placement part 5 has been structured as the conveyor belt including the belt 51 in the aforementioned embodiment, this is merely one example as the movable structure and another structure may be employed. The placement part 5 may be composed, for example, as a roller conveyor in which a roller is included in the placement surface 511. Further, in order to reproduce the walking on a slope, the actuator 6 may change the placement part 5 in such a way that the maximum inclination angle when the placement surface 511 of the placement part 5 is rotated toward the heel side of the sole frame 411 and the maximum inclination angle when the placement surface 511 of the placement part 5 is rotated toward the toe side of the sole frame 411 become the angle in accordance with the angle of the slope that is assumed. Further, the friction coefficient of the placement surface 511 of the placement part 5 may be arbitrarily set. Accordingly, the placement surface 511 having a friction coefficient that corresponds to the floor surface that is assumed may be used. By providing irregularities on the placement surface 511 of the placement part 5, walking on an undulating floor surface may be reproduced.

From the invention thus described, it will be obvious that the embodiments of the invention may be changed in many ways. Such variations are not to be regarded as a departure from the spirit and scope of the invention, and all such modifications as would be obvious to one skilled in the art are intended for inclusion within the scope of the following claims.

What is claimed is:

1. An evaluation apparatus comprising:
   a placement part on which a sole part of a walking assistance apparatus to be evaluated is placed;
   load applying means for applying a load to the walking assistance apparatus in a direction of the placement part in a state in which the sole part faces the placement part; and
   driving means for changing a relative positional relation of the placement part with respect to the sole part.

2. The evaluation apparatus according to claim 1, wherein the driving means changes a relative angle of the placement part and the sole part.

3. The evaluation apparatus according to claim 2, wherein the driving means changes the relative angle of the placement part and the sole part by changing an inclination angle of the placement part.

4. The evaluation apparatus according to claim 3, wherein the driving means changes the inclination angle of the placement part by swinging the placement part.

5. The evaluation apparatus according to claim 1, wherein a placement surface of the placement part comprises a movable structure.

6. An evaluation method for evaluating a walking assistance apparatus using a placement part on which a sole part of the walking assistance apparatus to be evaluated is placed, the method comprising:
   applying a load to the walking assistance apparatus in a direction of the placement part in a state in which the sole part faces the placement part; and
   changing a relative positional relation of the placement part with respect to the sole part.

7. The evaluation apparatus according to claim 1, wherein the placement part includes a rotatable placement surface configured to contact the sole part.

8. The evaluation apparatus according to claim 7, wherein the rotatable placement surface is a conveyor belt.

9. The evaluation apparatus according to claim 8, wherein the driving means changes a relative angle of the placement part and the sole part by changing an inclination angle of the placement part.

10. The evaluation apparatus according to claim 9, wherein a contact point between the sole part and the placement surface is moved on the placement surface when the placement part is inclined.

11. The evaluation method according to claim 6, wherein changing a relative positional relation of the placement part with respect to the sole part includes changing an inclination angle of the placement part.

12. The evaluation method according to claim 11, further comprising moving a contact point between the sole part and the placement surface when the inclination angle of the placement part is changed.

* * * * *